(12) United States Patent
Smith et al.

(10) Patent No.: US 9,322,785 B2
(45) Date of Patent: Apr. 26, 2016

(54) INCLUSION DETECTION IN POLISHED GEMSTONES

(75) Inventors: James Gordon Charters Smith, Buckinghamshire (GB); Graham Ralph Powell, Berkshire (GB)

(73) Assignee: De Beers UK Ltd., London (GB)

(*) Notice: Subject to any disclaimer, the term of this patent is extended or adjusted under 35 U.S.C. 154(b) by 880 days.

(21) Appl. No.: 13/505,314

(22) PCT Filed: Nov. 2, 2010

(86) PCT No.: PCT/EP2010/066641
§ 371 (c)(1),
(2), (4) Date: Jul. 11, 2012

(87) PCT Pub. No.: WO2011/054822
PCT Pub. Date: May 12, 2011

(65) Prior Publication Data
US 2012/0274751 A1   Nov. 1, 2012

(30) Foreign Application Priority Data
Nov. 3, 2009   (GB) .................................. 0919235.2

(51) Int. Cl.
*H04N 13/02* (2006.01)
*G01N 21/87* (2006.01)

(52) U.S. Cl.
CPC ...................................... *G01N 21/87* (2013.01)

(58) Field of Classification Search
CPC ................................ G01N 21/87; G01N 21/88
USPC ...................... 348/135, 61, 42, 50, 51, 52, 46; 434/386; 356/30; 382/154; 345/420; 63/32, 33, 26
See application file for complete search history.

(56) References Cited

U.S. PATENT DOCUMENTS

| 5,966,673 A | 10/1999 | Shannon, Sr. |
| 6,020,954 A | 2/2000 | Aggarwal |

(Continued)

FOREIGN PATENT DOCUMENTS

| CN | 1304035 A | 7/2001 |
| CN | 101118570 A | 2/2008 |

(Continued)

OTHER PUBLICATIONS

International Search Report for corresponding International Application No. PCT/EP2010/066641 mailed Mar. 2, 2011.

(Continued)

*Primary Examiner* — Jefferey Harold
*Assistant Examiner* — Jean W Desir
(74) *Attorney, Agent, or Firm* — Renner, Otto, Boisselle & Sklar, LLP

(57) ABSTRACT

A method and apparatus for generating a 3D model of and/or detecting inclusions in a polished gemstone such as diamond is described. The gemstone (103) is rotated in a series of discrete increments. At each rotational position of the gemstone, the gemstone (103) is illuminated with collimated light (111,112) and a silhouette image recorded. At each rotational position, the gemstone (103) is also (before further rotation) illuminated with diffuse light (109), and a diffuse image recorded. The images are analyzed to obtain a 3D model of the surface of the gemstone. Features may then be identified in the diffuse images and tracked between subsequent diffuse images. The tracked features may be located relative to the 3D model of the gemstone, taking into account reflection and refraction of light rays by the gemstone. Some or all of the located features may then be identified as inclusions.

34 Claims, 7 Drawing Sheets

(56) References Cited

U.S. PATENT DOCUMENTS

| | | | |
|---|---|---|---|
| 6,239,867 B1 | 5/2001 | Aggarwal | |
| 6,567,156 B1 | 5/2003 | Kerner | |
| 7,259,839 B2 | 8/2007 | Sivovolenko | |
| 2004/0246464 A1 | 12/2004 | Sivovolenko | |
| 2006/0062446 A1* | 3/2006 | Porat | G01N 21/87 382/154 |
| 2006/0066877 A1 | 3/2006 | Benzano | |
| 2007/0285650 A1 | 12/2007 | Kerner et al. | |
| 2010/0250201 A1* | 9/2010 | Sivovolenko | G01N 21/87 703/1 |
| 2012/0024010 A1* | 2/2012 | Maltezos | A44C 17/00 63/32 |
| 2014/0107986 A1* | 4/2014 | Sivovolenko | 703/1 |
| 2015/0022801 A1* | 1/2015 | Lapa et al. | 356/30 |

FOREIGN PATENT DOCUMENTS

| | | |
|---|---|---|
| CN | 101539530 A | 9/2009 |
| GB | 2 096 793 A | 10/1982 |
| JP | 11-352068 A | 12/1999 |
| JP | 2002-516992 A | 6/2002 |
| WO | 2006/033102 A1 | 3/2006 |
| WO | 2009/068354 A1 | 6/2009 |
| WO | 2009/133393 A1 | 11/2009 |

OTHER PUBLICATIONS

Written Opinion for corresponding International Application No. PCT/EP2010/066641 mailed Mar. 2, 2011.
British Search Report for corresponding British Application No. GB0919235.2 dated Feb. 25, 2012.
Harris et al., "A Combined Corner and Edge Detector", Alvey Vision Conference, Proceedings of the Alvey Vision Conference, Jan. 1, 1988, p. 147, XP001155775.
European Office Action for corresponding European Application No. 10 771 489.1 dated Jan. 16, 2015.
Chinese Office Action for corresponding Chinese Application No. 201080060278.8 issued Apr. 15, 2014 and English translation.
Japanese Office Action for corresponding Japanese Application No. 2012-537371 mailed Apr. 30, 2014 and English translation.

* cited by examiner

INCLUSION DETECTION IN POLISHED GEMSTONES

The present invention relates to 3D model generation and inclusion detection in polished gemstones. In particular, although not exclusively, the invention relates to inclusion detection in diamond gemstones.

The market value of a polished diamond depends on its colour, cut proportions, internal clarity and weight, known as the "Four Cs". It is relatively straightforward to determine the colour, cut and weight of a polished diamond, but clarity is generally more difficult to determine objectively. The clarity of a diamond is determined by the size, number and distribution of inclusions within it. The term "inclusions" is generally used in a broad sense, both herein and in the diamond industry, to cover cracks and other macro-defects, as well as inclusions of non-diamond material or other diamond crystals, that are visible under a given magnification, for instance ×10.

The internal clarity of the material may not be accurately assessed from external appearance using current methods. This is because the facility of seeing into the diamond is influenced by the refraction and scattering of light caused by the shape (cut) of the diamond.

Techniques for determining the external shape of a diamond have been established in the past. Such techniques typically involve the production of a series of images or silhouettes of a diamond obtained from many different directions. The images can then be combined to form a three dimensional map of the surface. Examples of such techniques are described in U.S. Pat. No. 4,529,305, U.S. Pat. No. 5,544,254, and U.S. Pat. No. 6,567,156. However, these documents do not provide information on determining the internal clarity of the diamond.

In principle, some of these limitations may be overcome by the technique of refractive index matching, where the object to be inspected is immersed in a cell containing a liquid of a similar refractive index to the material under inspection. For diamond, however, there are no suitable liquids to match its high refractive index (n=2.42). In addition, this is a complicated and labour intensive process and such liquids as are available are poisonous.

X-ray microtomography can provide information on both the external shape and internal properties of a diamond. The refractive index of diamond at these wavelengths is much closer to 1, and this facilitates the investigation of internal microstructure. An example of this is described by SkyScan (www.skyscan be/next/application0601.htm). However, the technique is too slow to be practical in many applications.

WO 02/46725 discloses an alternative method and apparatus for locating inclusions in a diamond. Each inclusion must first be identified by an operator. The diamond is then translated and rotated so that the inclusion is viewed from a number of different directions. Each time the translation and rotation is carried out an operator must identify the inclusion again. As a result the technique is again slow and impractical for automation.

Furthermore, the techniques described above are generally applicable to inclusion detection in rough (unpolished) stones. The behaviour of light within a polished stone is more difficult to model accurately, because there are many internal reflections at the facets of such stones.

It would be desirable to provide a technique capable of identifying inclusions and locating them automatically (i.e. without identification by an operator) in a polished gemstone. It would also be desirable to provide an improved technique for generating a 3D model of a gemstone.

In accordance with one aspect of the present invention there is provided a method for obtaining a 3D model of a gemstone. The method comprises rotating the gemstone in a series of discrete increments. At each rotational position of the gemstone, the gemstone is illuminated with collimated light and a silhouette image recorded. At each rotational position, the gemstone is also (before further rotation) illuminated with diffuse light, and a diffuse image recorded. The 3D model of the surface of the gemstone is obtained using information contained in the silhouette and diffuse images.

An initial 3D model may be obtained by analysis of the silhouette images. This initial model may then be refined using information contained in the diffuse images. The refinement may include aligning facet edges in the model with edges in the diffuse images, which may involve sampling an area in each diffuse image in a direction perpendicular to the initial model edge and finding a position of maximum gradient in a centre bar of the area.

The method may be extended for use in identifying inclusions. Features may be identified in the diffuse images and tracked between subsequent diffuse images. The tracked features may be located relative to the 3D model of the gemstone, taking into account reflection and refraction of light rays by the gemstone. Some or all of the located features may then be identified as inclusions. Indeed, this approach is possible using only the initial 3D model (obtained from the silhouette images), even if is not refined using the information contained in the diffuse images.

Since the silhouette images and diffuse images are obtained at the same rotational positions of the diamond (and preferably viewed by the same imaging means), the 3D model should match very closely the diffuse images used to track features.

The gemstone may be rotated about an axis generally perpendicular to a table facet of the gemstone. The images may be recorded by one or more cameras, and in one embodiment two cameras are used, at different poses relative to the axis of rotation of the gemstone.

The silhouette images may be recorded by a girdle camera generally directed towards the girdle of the gemstone. The diffuse images may be recorded by the girdle camera and a pavilion camera generally directed towards a pavilion of the gemstone.

It is advantageous for imaging system to provide an orthographic view, i.e. the imaging system may be telecentric in the object space so that in effect the viewpoint is at infinity.

In accordance with another aspect of the present invention there is provided a method of obtaining a 3D model of the surface of a gemstone. The method comprises analysing a set of silhouette images of the gemstone illuminated by collimated light obtained at a series of incremental rotational positions of the gemstone. Some of the silhouette images are identified as "key frames": a key frame is a silhouette image in which a plane of a facet of the gemstone is generally parallel to the axis of the camera so that said facet appears as a facet line in the silhouette image. In each key frame, a normal to the facet line is calculated. The normal to the facet line is in the plane of the image and corresponds to a normal to the facet in the 3D model.

For each silhouette image a convex hull may be identified bounding the pixels corresponding to the silhouette of the gemstone. On each convex hull, facet interface points may be identified corresponding to interfaces between facets on the gemstone. The variation may be monitored between subsequent images in the angle at each facet interface point. An image may be labelled as a key frame if the angle at a facet interface point is a maximum or a minimum. The line each side of the maximum or minimum facet interface point in the convex hull of a key frame may correspond to the facet line in that image.

Facet normals may initially be determined for crown facets and pavilion facets of the gemstone. The normal to a table facet of the gemstone may be calculated by identifying the axis of rotation of the gemstone. The other facets may be identified subsequently.

The 3D model may be refined by analysing diffuse images of the gemstone illuminated by diffuse light obtained at a series of incremental rotational positions of the gemstone.

The method of obtaining the 3D model may be used in the determination of inclusions described above.

In accordance with another aspect of the present invention there is provided a method of identifying inclusions in a gemstone. A 3D model of the surface of the gemstone is generated. A set of diffuse images of the gemstone illuminated by diffuse light obtained at a series of incremental rotational positions of the gemstone is analysed. Candidate features are identified in the images and tracked between adjacent images. For each tracked feature, a possible free-space position and refracted position relative to the 3D model are estimated. The calculation of the free-space position assumes that the feature is on a near surface of the gemstone so that light rays from a camera at which the image was obtained have not passed through the gemstone. The calculation of the refracted position assumes that the feature is within or at the back of the diamond so that light rays from the camera passed through the gemstone, the calculation taking into account reflection and refraction of light rays by the gemstone. Spurious features are filtered out, and inclusions corresponding to the refracted positions of features are identified. The free space position may be used to determine if a candidate feature lies on or outside the front surface of the gemstone (and therefore spurious).

Each tracked feature may be classified as an occlusion feature, surface feature, refracted feature, or erroneous feature, and only the refracted features used to identify inclusions. Other or additional classifications may be employed.

Spurious features generated by internal images may be identified as follows. In an image, a front facet may be conceptually pushed through the 3D model of the gemstone in the direction of a ray issuing from the camera and refracted through the front facet. The segments of back facets of the 3D model hit by the front facet as it is conceptually pushed through the model may be identified using a polygon-clipping algorithm. These segments, and the borders between them, may be identified in the front facet. The segments and borders seen in the front facet may then be classified as spurious features.

The segments may be then be conceptually reflected off the back facets and pushed through the model of the gemstone along the direction of the reflected ray.

Further facets hit, and segments of these facets visible in the front facet, may be identified using the polygon-clipping algorithm. The process may then be repeated up to a pre-defined maximum number of reflections, and all of the segments and borders between them identified as spurious features.

Features may then be clustered together to form defects. A bounding volume within the 3D model may be determined for each defect. Each bounding volume may be back-projected onto all the front facets through which it is visible. In each diffuse image, the grey-levels of pixels forming back-projections of each defect may be analysed, and statistical measures on the content of each defect obtained. The grey-levels of pixels may be determined relative to a map formed by the back projections of back facets of the gemstone. Parameters of the inclusions may be determined from the statistical measures.

The methods described above may be combined. Any of these methods may further comprise identifying the type, shape, size and/or density of the inclusions, and assigning a clarity value to the gemstone on the basis of the identified type, shape, size and/or density of the inclusions.

The gemstone may be a polished diamond.

The invention also provides apparatus for carrying out any of the methods described above, and a computer programme for effecting any of the analysis described.

In accordance with a further aspect of the present invention there is provided apparatus for generating a 3D model of a gemstone. The apparatus comprises a mounting stage for mounting the gemstone, the mounting stage being rotatable in a series of discrete increments. At least one camera is directed towards the mounting stage for recording images of the gemstone at each rotationally incremented position. A collimated light source is provided for illuminating the diamond with collimated light, and at least one diffuse light source is provided for illuminating the diamond with diffuse light. A control system co-ordinates the rotation of the mounting stage, operation of the light sources and operation of the at least one camera, so that the following steps are performed at each rotational position of the gemstone: (a) a silhouette image of the gemstone illuminated by collimated light is recorded by the camera; and (b) a diffuse image of the gemstone illuminated by diffuse light is recorded by the camera. A processing system is arranged to analyse the silhouette and diffuse images to obtain a 3D model of the surface of the gemstone. The processing system may be further arranged to generate an initial 3D model from the silhouette images and refine the model using the diffuse images.

The apparatus may also be usable to identify inclusions in the gemstone. The processing system may therefore be further arranged to identify features in the diffuse images, track the features between subsequent diffuse images, locate the features relative to the 3D model of the gemstone, taking into account reflection and refraction of light rays by the gemstone, and identify some or all of the located features as inclusions. The processing system may be arranged to use the initial 3D model (generated from the silhouette images only) in the identification of inclusions.

The apparatus may further comprise a stepper motor for rotating the mounting stage. Two or more cameras may be provided, at different poses relative to the axis of rotation of the mounting system. The cameras may include a girdle camera directed towards a girdle of a gemstone mounted on the mounting stage, arranged so that the silhouette images are recorded by the girdle camera, and a pavilion camera directed towards a pavilion of a gemstone mounted on the mounting stage.

Thus the apparatus of the present invention, at least in preferred embodiments, is designed to rotate a polished diamond, under several carefully controlled illumination conditions, and to capture images at regular, accurately determined angular increments around a highly stable axis of rotation. Images are captured by two cameras at different attitudes to the axis of rotation of the stone. The image sequences captured are processed to obtain an accurate solid model of the diamond, and optionally to track defects within the diamond. The tracks and solid model are then used together to position the defects at three-dimensional locations within the body of the stone model. These positions are further used to more closely examine the imagery with the aim of classifying particular identified defects in terms of severity and impact on the quality grade of the stone.

Some preferred embodiments of the invention will now be described by way of example only and with reference to the accompanying drawings, in which.

Figure 1:
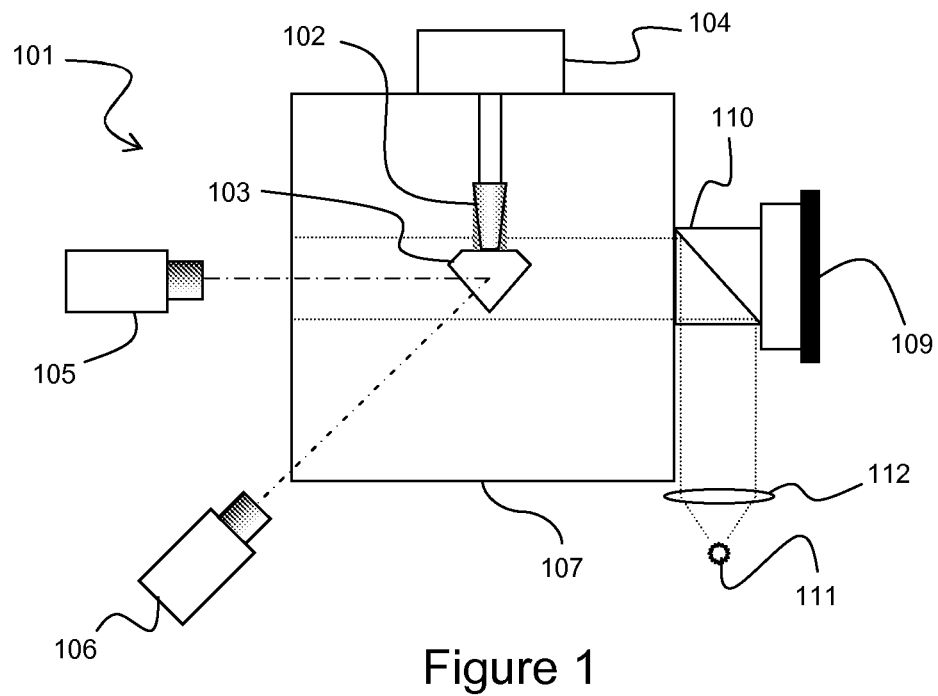
FIG. 1 is a top schematic view of an apparatus for illuminating a diamond and obtaining images at a range of rotational positions.
Figure 2:
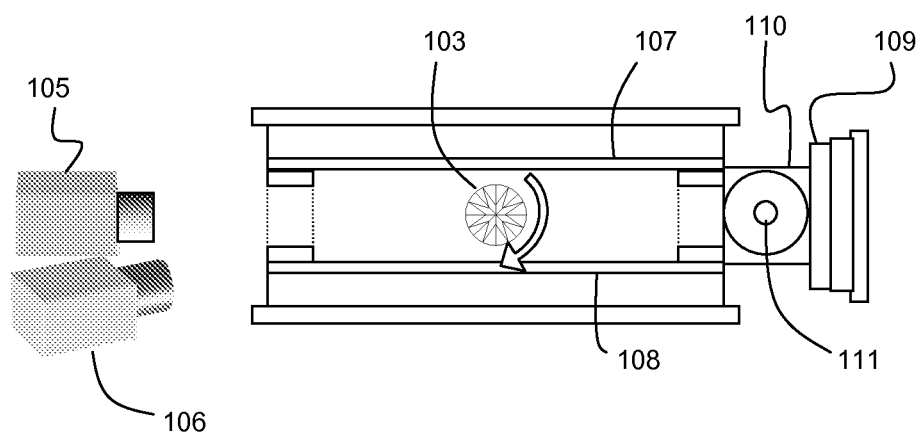
FIG. 2 is a side schematic view of the apparatus of FIG. 1.

FIGS. 1 and 2 are top and side views respectively of an apparatus 101 for determining the clarity of polished gemstones such as diamonds. The apparatus comprises a vacuum nozzle 102 onto which a diamond 103, or other object, can be placed. A stepper motor 104 is used to rotate the diamond 103 accurately through any specified angle.

Figure 3:
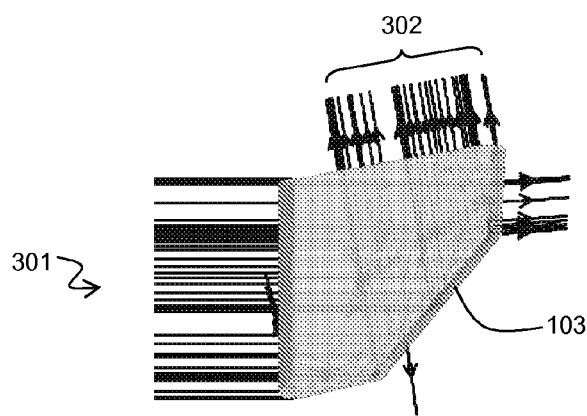
FIG. 3 is an illustration of the light path through a brilliant cut gemstone when illuminated through the pavilion.

Images of the diamond 103 are captured at each angular interval using two cameras 105, 106, such as for example single ½" (8 mm diagonal) CCD, IEEE1394-interfaced digital cameras with a resolution of 1280×960 pixels. The cameras are arranged such that one of them (the "girdle camera" 105) is directed at the girdle of the diamond 103 (i.e. "side on") and the other camera (the "pavilion camera" 106) looks directly into the pavilion facets of a typically cut diamond. Due to the way a diamond handles light, light rays reaching the camera will have been through the majority of the volume of the stone, and this view gives the best probability of any defect or inclusion being present in the images recorded by the cameras. This can be understood with reference to FIG. 3, which shows how light 301 passes through a diamond 103 and is reflected 302 towards a camera. The camera optics used are telecentric, i.e. they collect only light incident parallel to their optical axis within a range of angles determined by their numerical aperture. The images from the cameras are exported to a processing system and stored on a storage device (not shown in FIG. 1). These are used for subsequent analysis of the images.

The diamond can be illuminated by diffuse or collimated light, or both. Diffuse illumination is provided by three planar diffuse sources 107, 108, 109, in this case LED panels. Two larger panels 107, 108 are placed opposite each other with sufficient spacing to allow a diamond suspended on a nozzle to be placed between them. A third small panel 109 has twice the intensity of the large panels. This is behind a beam splitter 110, which is used to either introduce collimated light or diffuse light, as shown in FIG. 1. Collimated light is provided by a further LED 111 and associated optics 112.

Figure 4:
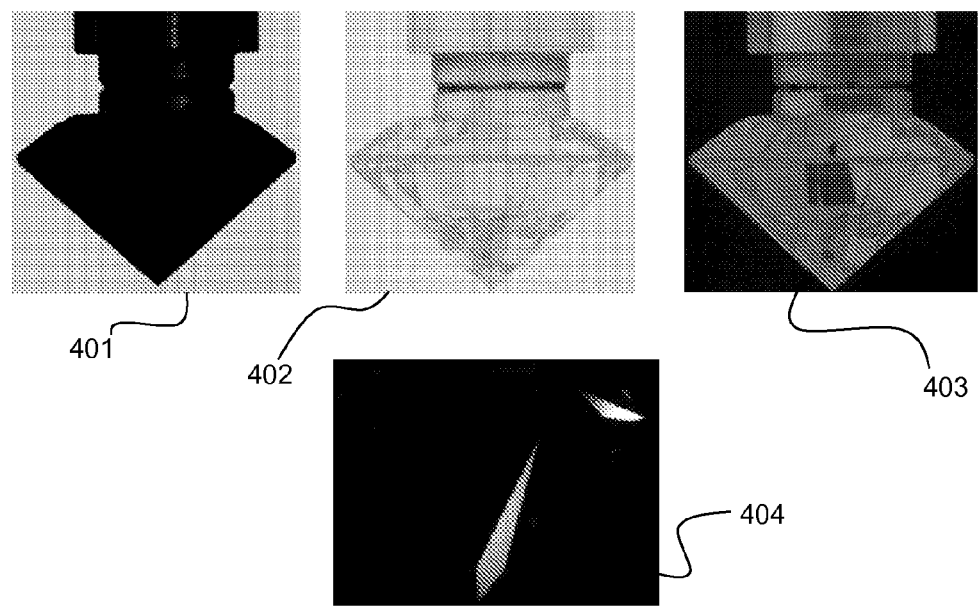
FIG. 4 is a series of photographs of a diamond illuminated according to different schemes.

The apparatus is designed to produce four different lighting schemes. The optical and mechanical arrangement of the different light sources allows each lighting condition to be produced without compromising the others. The four lighting types are collimated, diffuse, semi-diffuse and specular, and images of a diamond using these four schemes are illustrated in FIG. 4. Collimated lighting (provided by the LED 111 and optics 112) allows the diamond to be seen completely in silhouette (image 401); diffuse lighting (approaching $4\pi$ steradians of white light) causes defects on, and inside, the diamond to be visible (as shown in image 402). Semi diffuse illumination is where the diamond is lit from behind and one side or just one side and can be used to highlight the facet structure of the diamond (as shown in image 403). The fourth lighting condition is specular lighting and this allows front facets to be highlighted individually (image 404). This condition also highlights the facet structure of the diamond and can be used in place of the semi-diffuse illumination for diamond model refinement.

For accurate measurements to be made from the imagery it is extremely important to know the positions of the cameras relative to each other and also to the axis of rotation of the object (diamond). It is also important that the exact angle of rotation, around the axis, is known between each image capture since any motor used to rotate the nozzle is unlike to have exact angular accuracy.

Figure 5:
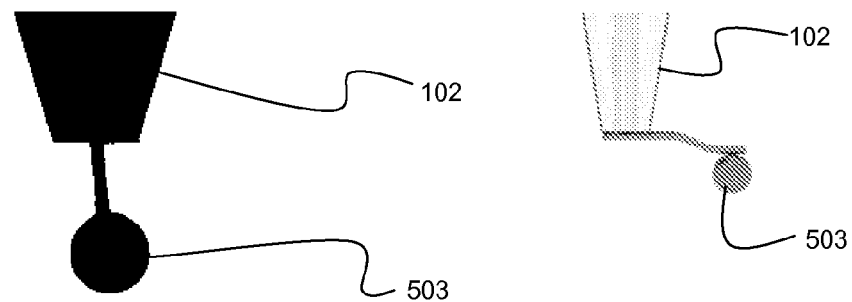
FIG. 5 illustrates a calibration target.

The characterisation of the rotational axis is achieved by mounting a target on the nozzle in place of the diamond, the mounting being eccentric from the axis of rotation. This is illustrated in FIG. 5. In this example, the target is a ball bearing 503. Images of the target in silhouette are obtained with the two cameras around several complete rotations. These are repeated with the ball at at-least two starting positions differing by approximately 90 degrees around the axis of the rotation.

Figure 6:
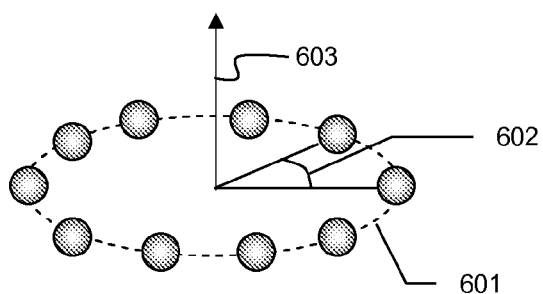
FIG. 6 illustrates the principle of mechanical calibration.

The position of the centre of the ball bearing can be determined extremely accurately from the silhouette images. By observing the path taken by the centre of the ball bearing, the axis of rotation with respect to the cameras can be determined. The spacing of the measured centres between images can be used to map the angular increments of the motor mapped, as shown in FIG. 6. FIG. 6 illustrates the locus 601 of the ball 503 at regular angular increments 602 around the axis of rotation 603.

Once the apparatus is mechanically calibrated, a diamond or other gemstone is mounted on the vacuum nozzle, and measurement is carried out. The measurement has several stages:

1. Image capture sequence.
2. Extremely accurate shape measurement and stone model generation using silhouette imagery, further refined with specular and/or diffuse/semi-diffuse imagery.
3. Defect detection and tracking.
4. Back projection of light paths through the stone which allows the determination of positions of internal edges.
5. Defect clustering.
6. Identification of bounding areas of defects in diffuse imagery and statistical measures of defects within these areas.
7. Classification of defects to assess severity and assignment of grade to stone.

These stages will now be described in more detail.

1. Image Sequence Capture

The vacuum nozzle to which the diamond is attached is rotated in discrete increments by the stepper motor. After each incremental rotation, images are captured under all illumination conditions by both cameras. Ideally, the diamond should undergo only a single complete rotation: the different illuminations should be applied sequentially at each rotational position to avoid any errors being introduced by movements which might occur between multiple rotations. In other words, following each incremental rotation, all of the required images under all the lighting conditions (silhouette, diffuse, partially diffuse and specular) are recorded by both cameras before the next incremental rotation is effected.

This process results in a complete set of images being obtained for the diamond at all rotational positions. Analysis can then be carried out on these images.

2. Shape Measurement

For the raytracing and modelling of internal edges that occurs later in the process, an extremely accurate model of the target object is needed. This is obtained by analysis of the silhouette images obtained by the girdle camera (i.e. images obtained when the diamond is illuminated only by collimated light), which can be considered as a series of frames. This analysis begins with the determination of normal vectors from the facets of the diamond. The measured normals are input into an algorithm that outputs the smallest 3D convex shape consistent with them.

Finding the Convex Hull

Figure 7:
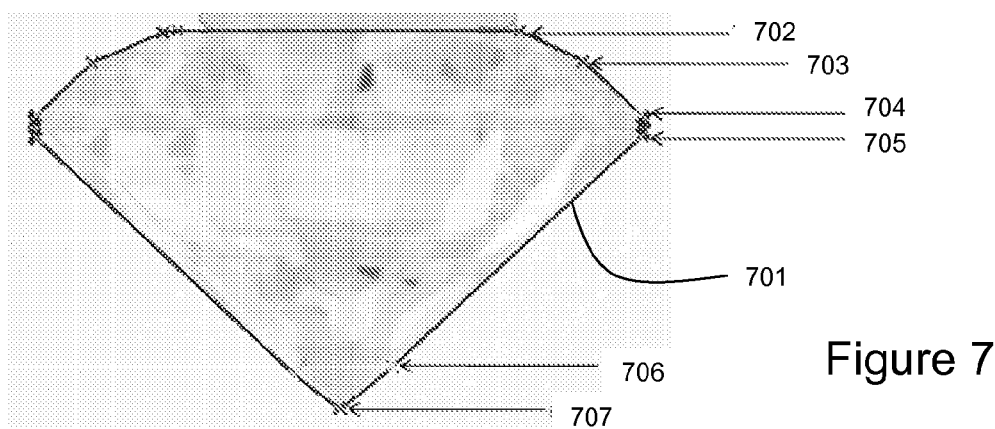
FIG. 7 is a photograph of a diamond illustrating the convex hull.

In order to find the facet normal vectors, the first step is, for each girdle silhouette frame, to identify the convex hull around the silhouette of the diamond (a convex hull is a convex polygon whose vertices are some of the points in the input set). The convex hull is identified by taking the left most silhouette point in the frame and then walking such that the next point on the convex hull is the silhouette point that creates the greatest angle. A convex hull 701 determined by this method is illustrated in FIG. 7. The convex hull includes a series of points (table point 702, crown point 703, upper girdle point 704, lower girdle 705, pavilion point 706, and culet point 707) marking the interfaces between facets.

Measuring Facet Normals

Figure 8:
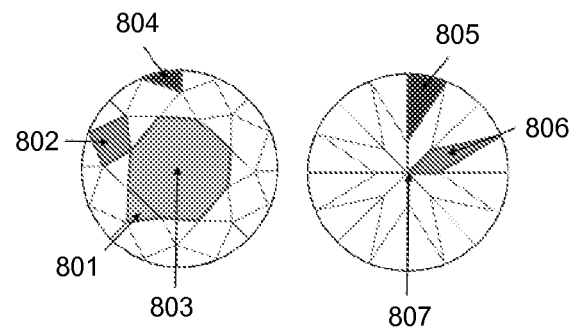
FIG. 8 illustrates the principal facets of a brilliant cut diamond.

Facet normals are obtained for principal facets first. Extra facets are then added in as necessary. FIG. 8 illustrates the principal facets of a typical diamond seen from above and below: star facets 801, kite facets 802, table facet 803, upper girdle facets 804, lower girdle facets 805, pavilion main facets 806 and culet 807. Once the normals of the principal facets have been obtained, the convex object generation algorithm has enough information to make an initial determination of the shape of the diamond, which can be subsequently refined.

The facet normals of the principal crown facets (star and kite facets 801, 802 in FIG. 8) and pavilion facets (pavilion main facets 803 in FIG. 8) are found by taking measurements on the silhouette imagery on "key frames". As the diamond is rotated, the apparent angle in the convex hull between facets (at the crown point 703, pavilion point 706 etc. shown in FIG. 7) varies. A key frame is defined to be a frame in which the change in angle in the convex hull at a pavilion or crown point is at a minimum (i.e. flat) or at a maximum. There are two sets of these key frames, crown and pavilion, to allow for misalignment of the two parts of the stones. Crown key frames are found by considering the angle formed by the two straight edges of the convex hull either side of the crown point. "Minimum crown key frames" are found where this angle is at a local minimum. Similarly, "maximum crown key frames" are found by determining the peak angle. The key frames are those which are closest to these peaks. The normals to the kite and star facets are the lines perpendicular to the convex hull, in a key frame, of the kite and star facets measured.

Figure 9:
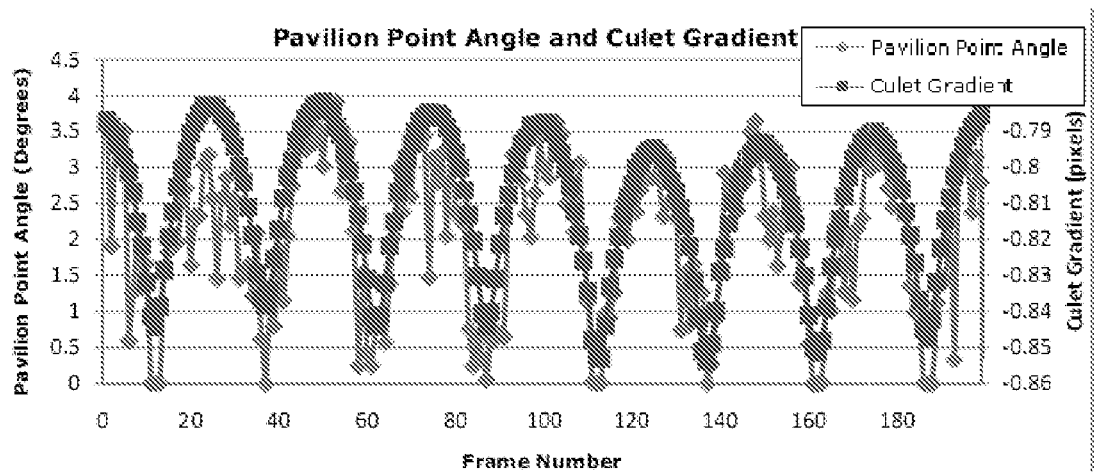
FIG. 9 illustrates how the culet gradient and pavilion point angle vary with rotational position.

A similar method is used to find Pavilion key frames. However because the measurement of the angle either side of the pavilion point is too noisy to interpolate to reliably, the angle between the pavilion facets at the culet point is used instead. FIG. 9 illustrates the behaviour of the pavilion point and culet point between frames.

Although the girdle of the diamond is not necessarily faceted it is approximated as a series of facets on the generated model. The normals of these facets are found by measuring the normal to the most vertical section between the two girdle points.

The upper and lower girdle facets are never viewed perpendicularly in any of the key frames. Instead, one of their edges is seen in these frames. Therefore, a point based method is used for these facets. Measurements of the observed edge between the upper girdle point and crown point on the convex hull of a minimum crown key frame are used to determine two points. A measurement of the upper girdle convex hull point on the adjacent maximum crown key frame is used to determine a third point on the upper girdle facet plan and from these three measurements the facet normal is determined. A similar approach is used to determine the lower girdle facets from minimum and maximum pavilion key frames The table facet normal is determined by assuming it is in the same orientation as the axis of the nozzle on which the diamond is suspended.

Once the principal facet normals have been measured, a 3D model can be generated using a convex shape generation algorithm. This generated model can then be refined so that the model facet edges best align with the diamond edges in the images, as described in more detail below. However, if the diamond contains additional facets (which are not principal facets), the model outline will still not fit the convex hull in the areas where the extra facets are present.

Every pixel inside the generated model projection has an associated distance which is approximately the perpendicular distance of the pixel from the model outline. If the perpendicular distance of the convex hull to the pixels it contains is greater than a threshold distance an extra facet is calculated and inserted into the model.

Refinement of the Model

Since it is only the key frames that are used in the generation of the model, the facet normals can contain significant errors. These errors can be reduced by refining the model so that the facet edges align with edges in the diffuse or part-diffuse images (the images obtained when the diamond is illuminated using diffuse light). A model refinement algorithm adjusts facet normals so that the model edges align with the edges in the corresponding specular, diffuse or semi-diffuse imagery.

Measurements are taken in every frame at control points along each of the edges which are at the front of the diamond in that frame. For each control point the measured position in the imagery is found by sampling an area of pixels in a direction perpendicular to the model edge and finding the position of maximum gradient in the centre bar.

Measuring edges in diffuse imagery is more complicated than in the specular imagery. This is because the diffuse imagery contains both the front edges and the edge segments that are seen reflected and refracted through the diamond. Therefore, it is possible that the measurement of a particular control point could be seduced by the wrong edge, which would pull the refinement minimisation out. Several methods are used to aid with this problem:

The orientation of the model and measured edge are considered. If the orientations are too different, the measurement is rejected.

A measurement is rejected if there is a second edge whose contrast is greater than a specified fraction of the strongest edge and within a specified pixel distance from this edge.

Any measurements which are greater than a threshold distance from the modelled edge are removed from the minimisation. The threshold used for this removal is reduced every iteration so that the constraint is tightened as the model edges get closer to the measurements.

Given a modelled point, p, on the image and a modelled edge direction, e, the following algorithm (illustrated in FIG. 10) is used to find the corresponding measurement, m, of the edge in the diffuse or part-diffuse imagery.

Figure 10:
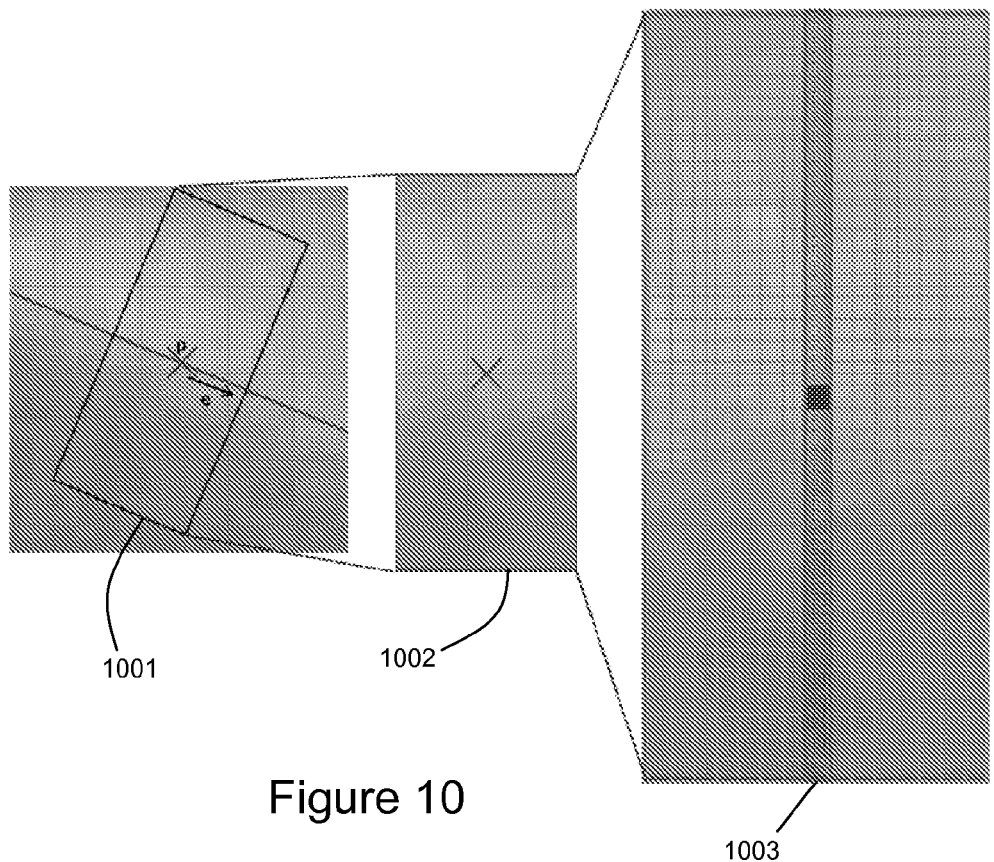
FIG. 10 illustrates an edge in a diffuse image.

1. Sample a bar 1001 of ±y pixels at half pixel intervals from p in the direction perpendicular to e. Take such samples at ±x pixels at half pixel intervals in the direction of e. This gives an array 4x+1 bars of 4y+1 samples 1002 (as can be seen in FIG. 10). If the modelled edge is parallel to the measured edge, the measured edge should be horizontal in this bar array.
2. Smooth the bar array horizontally (i.e. parallel to the edge)
3. For each bar 1003,
   A. Find the bar gradient magnitude at each sample
   B. Find the best and second best peak by finding the maximum and second maximum gradient magnitudes.
   C. If the second maximum gradient magnitude is at least 75% as strong as the maximum gradient magnitude and is within a threshold number pixels of the maximum then a second candidate edge is recorded.
4. If measuring the front of the tube:
   A. Set the mid peak position to be the median peak position across all bars.
5. If measuring model edges:
   A. Fit a straight line to the peak positions. If the gradient of this line is <−0.1 or the gradient is >0.1 (i.e. the angle is more than ~5.7° from horizontal) then reject the measurement.
   B. If a second candidate edge is recorded, then reject the measurement.
   C. Otherwise set the mid peak position to be the best peak on the middle bar
6. Linearly interpolate the samples around the mid peak to get the sub-sample position of the edge position.

Figure 11:
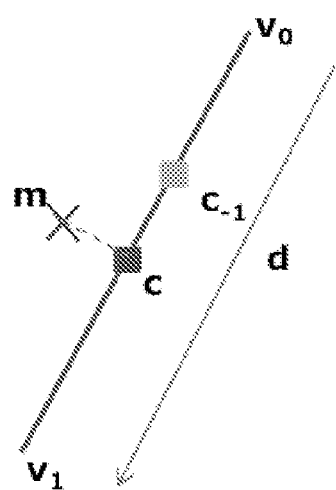
FIG. 11 illustrates the correction of a measured point compared to a control point.

Given a measured pixel position and a projected model edge, it is useful to find where on the edge the control point now lies such that the measurement lies down the perpendicular to the edge from this control point (see FIG. 11).

Let $V'_0$, and $V'_1$ be two vertices on the edge. These can be transformed into camera coordinates and projected onto the image to give pixel positions, $v_0$, and $v_1$.

The direction of the projected edge is d:

$$d = v_1 - v_0$$

It can be determined how far up the edge the pixel measurement, m, is. This proportion along the line $\overrightarrow{v_0 v_1}$ is λ and is calculated as:

$$\lambda = \frac{(m - v_0) \cdot d}{|d|^2}$$

The new control point's pixel position is then, c:

$$c = v_0 + \lambda d$$

It is now possible to determine the new control point's model coordinates, C, thus:

$$C = V_0 + \lambda(V_1 - V_0) = V_0 + \left(\frac{(c_{-1} - v_0) \cdot d}{|d|^2}\right)(V_1 - V_0)$$

where $c_{-1}$ is the old control point pixel position.

3. Defect Detection, Tracking and 3D Plotting

Defect tracking is carried out by analysis of the diffuse images obtained by both the girdle camera and the pavilion camera. Since the positions of the two cameras relative to each other is known, it is possible to relate the images obtained by both cameras directly to the 3D model previously obtained.

Using the diffuse imagery, an implementation of the Harris corner detector (as described in C. Harris and M. J. Stephens, "A combined corner and edge detector", Alvey Vision Conference, pages 147-152, 1988) may be used to identify candidate features in an image which could possibly be defects. A 2D tracking algorithm is then used to attempt to find a matching corners in adjacent frames in the image sequence that are then grown into "tracks". Once a feature has been tracked over a number of frames it is then possible to estimate a 3D position for the feature within the diamond volume using the camera and model geometry. Two 3D positions are estimated, one assuming the feature is on the near surface of the diamond, and has been seen only through free-space (free-space position), and the other assuming the feature has been seen through the diamond (refracted position). In order to estimate the refracted position, the rays from the cameras to the observations treated as though they have been refracted and reflected through the diamond.

Figure 12:
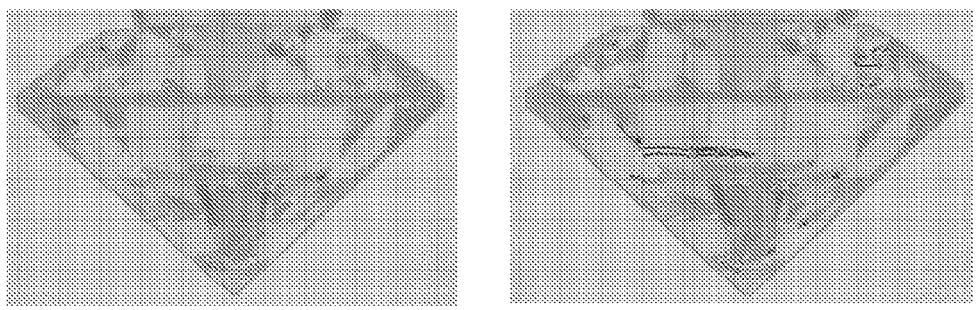
FIG. 12 shows extracted corner features and tracks of corner features in a photograph of a diamond.
Figure 13:
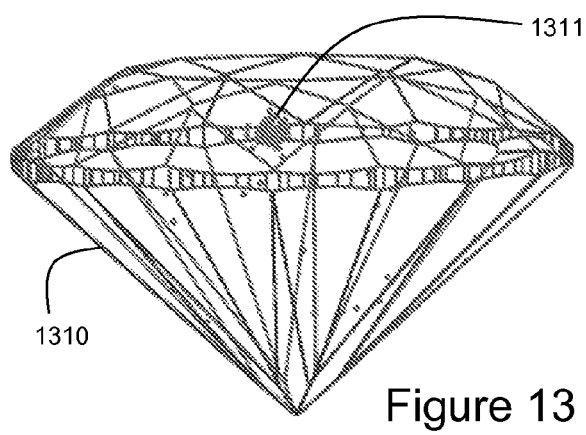
FIG. 13 illustrates position estimates of tracked features in a 3D model of a diamond.

FIG. 12 shows two photographs of a diamond, illustrating extracted corner features and tracks of corner features. FIG. 13 illustrates a 3D model of a diamond 1310 showing the position estimates of tracked features 1311 within the model.

It is not only features on defects that are tracked. Often, there are other spurious features, such as those caused by the sliding of two planes over each other. These features need to be classified and filtered out before any attempt at clustering is made. This is aided by determining the positions of internal edges (as described in the next section).

Track are classified into four possible types:
Occlusion tracks—formed by one surface sliding in front of another
Surface tracks (on the diamond front surface)
Refracted tracks (including reflected, interior to the diamond)
Not accepted tracks (i.e. erroneous)

Features on, or close to, the surface of the diamond nearer to the camera need to be distinguished from features seen through the diamond. This is because a surface feature's real position is its free-space position, whereas if a feature is seen through the diamond, its real position is its refracted position. If a surface feature has a position just in front of the near surface, its refracted position will be further away from the diamond surface.

A feature is classified as being a surface feature if satisfies all of the following criteria:

it is not an occlusion feature;
it is longer than a threshold;
its free-space RMS error is below a threshold; and
it is either in front of the near surface, or very close to the near surface.

Most tracked features are seen through the diamond and should be classified as refraction features. Refraction features are those satisfying all of the following criteria:

they are not already classified as occlusion or surface features;
are longer than a certain threshold; and they
have a refracted RMS error lower than a second threshold.

Finally, all remaining tracked features (i.e. those that have not been classified as occlusion, surface, or refracted) are said to be erroneous and are not accepted.

4. Determining the Positions of Internal Edges

Figure 14:
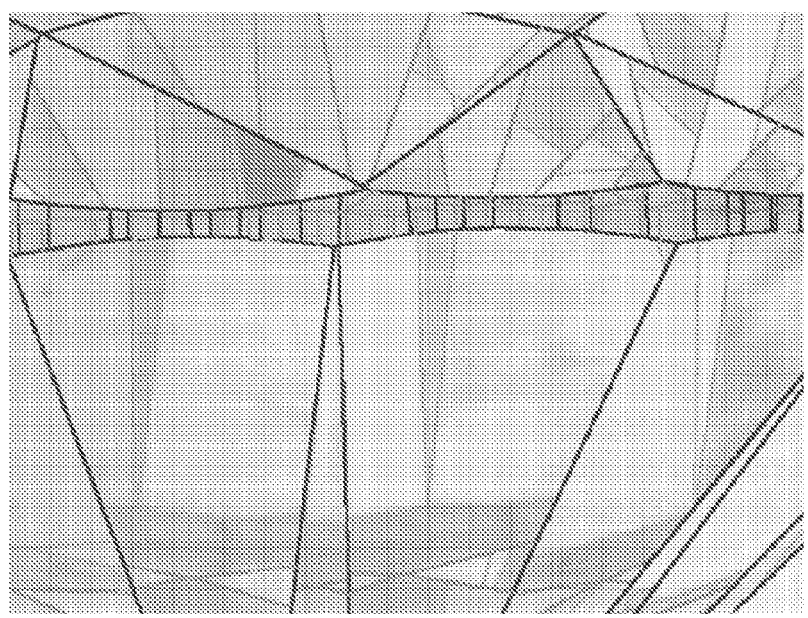
FIG. 14 illustrates back projected facet edges of a diamond.

The diamond model determined from the silhouette analysis is also used to raytrace facet edges, as shown in FIG. 14. These edges are used in the subsequent processes to determine whether defect observations are likely to be artifacts of the scene clutter produced by the diamond facets. This decision is made after clustering is performed.

On a particular frame, each front facet is conceptually pushed through the diamond in the direction of the ray that comes from the camera and is then refracted through the front facet. This facet hits a number of back facets. The segments of these back facets that are seen through the front facet are determined by using a polygon-clipping algorithm.

These facet segments are then reflected off the relevant back facet and pushed through the diamond in the direction of the reflected ray. The facets that are hit, and segments of these facets that are visible, can then be determined by again using the polygon clipping (the Weiler Atherton) algorithm. This process can continue up to a pre-defined maximum number of reflections.

The result is a set of polygons that are visible through the front facets on a frame. An example can be seen in FIG. 14. These polygons are used in the process of defect analysis to determine the background grey-level in a particular area.

5. Defect Clustering

Figure 15:
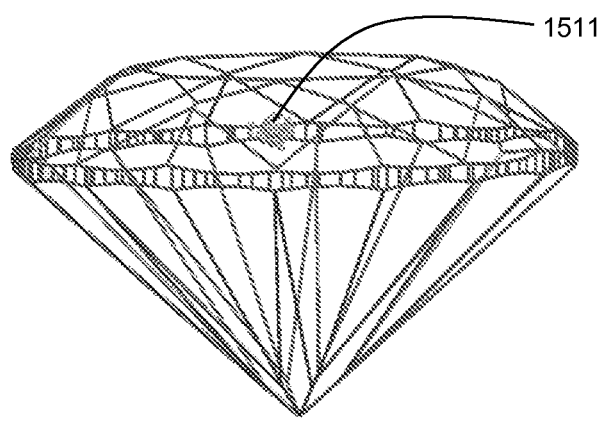
FIG. 15 illustrates clustered tracks in a 3D model of a diamond.

Defects come in many shapes and sizes. Therefore, the corner detector can find many trackable features on a single large defect. As a result, a large defect can produce a cloud of tracked features (as shown in FIG. 13). It is useful to associate these clouds of features, in order to produce a single entity 1511 per defect, as shown in FIG. 15. These clusters, and the features contained within them, can then be analysed to determine the attributes (such as size, shape and density) of the defects.

Three clustering techniques, based on different metrics, have been developed: Euclidian; Mahalanobis; and grey-level. Euclidean clustering associates all tracks that are less than a threshold distance away from each other (in Cartesian space). Mahalanobis clustering merges clusters whose Mahalanobis distance is less than a threshold. Grey-level clustering looks for pairs of observations, which are seen through the same facet on the same frame, and merges the corresponding clusters if it is decided the two tracks are on the same defect. This decision is based upon whether the pixels, on the image, remain dark between the two observations.

6. Diffuse Imagery Re-Examination/Defect Analysis

In order to analyse the content of the defects, the grey-levels in the diffuse images are considered. To determine the areas on a frame that contain parts of the defect, the bounding volume of the defect cluster is back-projected onto all the front-facets through which it was observed. The grey-levels of pixels within these front facets are then considered and statistical measures on the content of the defect obtained.

Back Projection of Cluster Bounding Volume

Every tracked feature in a cluster is labelled with the facet it has been seen through and the facets from which it has been seen reflected. This is the path of a track. Combining the track paths from a cluster is used to determine frames on which the cluster has been observed.

Figure 16:
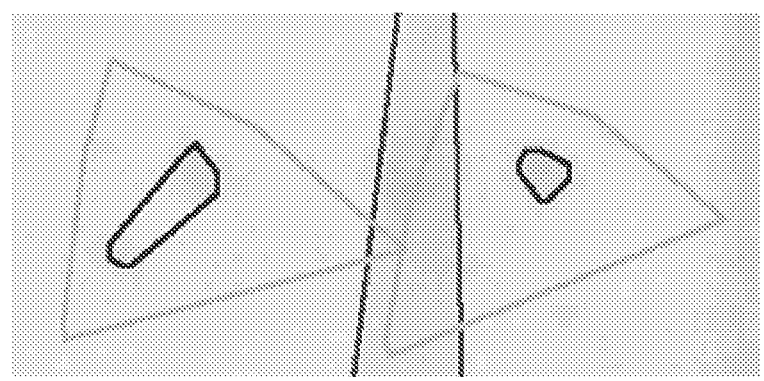
FIG. 16 illustrates a projection of the bounding volume of defect in an image of a diamond.

For each of the combined paths or cluster observations the 3D track positions are projected onto the relevant image frames, and a convex hull drawn around them which effectively results in a projection of the bounding volume of the cluster on those frames, as shown in FIG. 16.

Every frame now has a list of cluster observations and their associated projected bounding volumes. For each frame that contains a cluster observation, the front facets through which a cluster has been seen are considered and the pixel-based densities within these front facets determined.

Determining Individual Defect Pixel Density

The amount by which the pixel is darkened is relative to the intensity the pixel would have been if no defect were present. This intensity is approximated by finding the local median pixel grey-level in the appropriate patch. This local estimation of the background at a pixel is subtracted from the pixel grey-level, and the result divided by the background estimation, to get an approximation of the density value at the pixel.

The constant intensity areas of background are determined by back-projecting the internal edges as previously described. The output of this process is a set of polygons seen through a front facet on a frame. The back projected polygons are drawn onto a polygon label images so that it is possible to look up directly on which polygon a pixel lies.

The grey-levels of pixels within projected volumes on the front facets are then considered and statistical measures on the content of the defect obtained.

Improving the Projected Bounding Volume

The bounding volume for a given cluster can be much smaller (or much larger) than the part of the defect visible in a frame. This may be due to track observational inaccuracies and only certain parts of the defect being tracked. Once the estimation of the pixel density for every pixel within a facet has been calculated, it is possible to refine the shape of this bounding area to match the imagery much better.

The pixel, whose density is below an adjustable threshold and contained in a projected bounding volume are flood-filled using an intelligent flood-filling algorithm that is guided by the internal edges and projected bounding volumes. The flood filled area needs to be clipped by the facet edges that have a shorter path than the cluster observation. Therefore a pixel is only flood filled if the facet polygon it lies in has the same path as the cluster observation.

A convex hull is drawn around all of the flood-filled areas for a cluster observation to get the improved bounding area. The pixels within this area are used to accumulate the statistical evidence for the defect.

Analysing Defects Using Pixels within the Bounding Area

Pixels within the cluster observation bounding areas are considered and analysed to produce some overall statistics for the defect. These statistics include:

the average pixel size of the defect;
the average density of the defect;
the shape of the defect with regards to whether it is a single dense mass or several smaller dense 'blobs'.

A median frequency histogram of pixel density values is calculated. Instead of each bin containing the weighted number of pixels of the density, this histogram contains the median weighted number of pixels of the density. The median is used in order to filter out spurious cluster bounding areas.

Analysing the Histograms

Once the histograms have been accumulated, the statistics described in the table below are obtained. These statistics can be used to determine further measures. For example, the total amount of dense material within a defect can be found by multiplying the median density with the median size. The degree to which the defect is a solid blob is determined by comparing the darkness and gappiness measures.

| Statistic | Description |
| --- | --- |
| Median size | The median size of the defect (in pixels) |
| Histogram position threshold | The position chosen to divide the density median histogram into classified as either dark or gap. |
| Defect peak position | The position of the peak of the density median histogram. |
| Modal density | The defect peak position expressed as a fraction of 256. |
| Median density | The 50%-ile in the density median histogram, expressed as a fraction of 256. |
| Mean density | Mean bin position in the density median histogram, expressed as a fraction of 256. |
| Darkness | The fraction of pixels below the histogram position threshold. |
| Gappiness | The fraction of pixels above the histogram position threshold. |

Additional or other measures may be employed.

7. Classification of Defects.

Using the statistical measures produced, together with the locations of the defects within the diamond, it is then possible to produce a classifier measuring the severity of the detected defects and ultimately relating these to the quality grade of the stone.

It will be appreciated that variations from the above described embodiments may still fall within the scope of the invention. For example, the discussion refers to measurement and analysis of diamonds, but it will be appreciated that the system could be used to determine the clarity of other gemstones.

In addition, the system described above includes stopping the rotation of the diamond at regular angular intervals, in order to capture images. Another approach could be to rotate the stone at a known angular velocity, pulse the illumination and trigger the cameras at regular intervals in order that images are captured at equal angular separation. The illumination could be pulsed sequentially (collimated, diffuse, semi-diffuse etc.) in order that only a single rotation of the stone is required. Other schemes will also be apparent to one skilled in the art.

The invention claimed is:

1. A method for obtaining a 3D model of a gemstone, comprising:
   rotating the gemstone in a series of discrete increments;
   performing the following steps at each rotational position of the gemstone:
   (a) illuminating the gemstone with collimated light;
   (b) recording a silhouette image of the gemstone based on the collimated light;
   (c) illuminating the gemstone with diffuse light; and
   (d) recording a diffuse image of the gemstone based on the diffuse light;
   analysing the silhouette images to obtain an initial 3D model of the surface of the gemstone; and
   refining the initial 3D model using information contained in the diffuse images to obtain the 3D model.

2. The method of claim 1, further comprising aligning facet edges in the initial model with edges in the diffuse images.

3. The method of claim 2, further comprising sampling an area in each diffuse image in a direction perpendicular to the initial model edge and finding a position of maximum gradient in a centre bar of the area.

4. A method of detecting inclusions in a gemstone, comprising:
   generating a 3D model of the gemstone using the method of claim 1;
   identifying features in the diffuse images;
   tracking the features between subsequent diffuse images; and
   locating the features relative to the 3D model of the gemstone, taking into account reflection and refraction of light rays by the gemstone; and
   identifying some or all of the located features as inclusions.

5. The method of claim 1, wherein the gemstone is rotated about an axis generally perpendicular to a table facet of the gemstone.

6. The method of claim 1, wherein the silhouette images are recorded by a girdle camera generally directed towards a girdle of the gemstone.

7. The method of claim 1, wherein the diffuse images are recorded by the girdle camera and a pavilion camera generally directed towards a pavilion of the gemstone.

8. The method of claim 4, wherein the step of identifying some or all of the features as inclusions is carried out using a method of identifying inclusions in a gemstone, comprising:
   generating a 3D model of the surface of the gemstone;
   analysing a set of diffuse images of the gemstone illuminated by diffuse light obtained at a series of incremental rotational positions of the gemstone;
   identifying candidate features in the images;
   tracking the features between adjacent images;
   for each tracked feature, estimating a possible free-space position and refracted position relative to the 3D model, wherein:
      the calculation of the free-space position assumes that the feature is on a near surface of the gemstone so that light rays from a camera at which the image was obtained have not passed through the gemstone; and
      the calculation of the refracted position assumes that the feature is within or at the back of the diamond so that light rays from the camera passed through the gemstone, the calculation taking into account reflection and refraction of light rays by the gemstone;
   filtering out spurious features; and
   identifying inclusions corresponding to the refracted positions of features.

9. The method of claim 4, further comprising identifying the type, shape, size and/or density of the inclusions, and assigning a clarity value to the gemstone on the basis of the identified type, shape, size and/or density of the inclusions.

10. The method of claim 1, wherein the gemstone is a polished diamond.

11. Apparatus for carrying out the method of claim 1.

12. A method of obtaining a 3D model of the surface of a gemstone, comprising:
   analysing a set of silhouette images of the gemstone illuminated by collimated light obtained at a series of incremental rotational positions of the gemstone;
   identifying each silhouette image in which a plane of a facet of the gemstone is generally parallel to the axis of the camera so that said facet appears as a facet line in the silhouette image, and labelling such images as key frames; and in each key frame, calculating a normal to the facet line, the normal to the facet line in the plane of the image corresponding to a normal to the facet in the 3D model.

13. The method of claim 12, further comprising:
for each silhouette image, identifying a convex hull bounding the pixels corresponding to the silhouette of the gemstone;
on each convex hull, identifying facet interface points corresponding to interfaces between facets on the gemstone;
monitoring the variation between subsequent images in the angle at each facet interface point; and
labelling an image as a key frame if the angle at a facet interface point is a maximum or a minimum.

14. The method of claim 13, wherein the line each side of the maximum or minimum facet interface point in the convex hull of a key frame corresponds to the facet line in that image.

15. The method of claim 13, wherein facet normals are determined for crown facets and pavilion facets of the gemstone.

16. The method of claim 15, further comprising calculating the normal to a table facet of the gemstone by identifying the axis of rotation of the gemstone.

17. The method of claim 12, further comprising refining the 3D model by analysing diffuse images of the gemstone illuminated by diffuse light obtained at a the series of incremental rotational positions of the gemstone.

18. A method for detecting inclusions in a gemstone, comprising:
rotating the gemstone in a series of discrete increments;
performing the following steps at each rotational position of the gemstone:
 (a) illuminating the gemstone with collimated light;
 (b) recording a silhouette image of the gemstone based on the collimated light;
 (c) illuminating the gemstone with diffuse light; and
 (d) recording a diffuse image of the gemstone based on the diffuse light;
analysing the silhouette images to obtain a 3D model of the surface of the gemstone;
identifying features in the diffuse images;
tracking the features between subsequent diffuse images; and
locating the features relative to the 3D model of the gemstone, taking into account reflection and refraction of light rays by the gemstone; and
identifying some or all of the located features as inclusions.

19. A method of identifying inclusions in a gemstone, comprising:
generating a 3D model of the surface of the gemstone;
analysing a set of diffuse images of the gemstone illuminated by diffuse light obtained at a series of incremental rotational positions of the gemstone;
identifying candidate features in the images;
tracking the features between adjacent images;
for each tracked feature, estimating a possible free-space position and refracted position relative to the 3D model, wherein:
 the calculation of the free-space position assumes that the feature is on a near surface of the gemstone so that light rays from a camera at which the image was obtained have not passed through the gemstone; and
 the calculation of the refracted position assumes that the feature is within or at the back of the diamond so that light rays from the camera passed through the gemstone, the calculation taking into account reflection and refraction of light rays by the gemstone;
filtering out spurious features; and
identifying inclusions corresponding to the refracted positions of features.

20. The method of claim 19, wherein the free space position is used to distinguish spurious features on or outside the surface of the gemstone from internal objects.

21. The method of claim 19, wherein each tracked feature is classified as an occlusion feature, surface feature, refracted feature, or erroneous feature, and only the refracted features are used to identify inclusions.

22. The method of claim 19, wherein spurious features generated by internal images are identified by:
in an image, conceptually pushing a front facet through the 3D model of the gemstone in the direction of a ray issuing from the camera and refracted through the front facet;
identifying the segments of back facets of the 3D model hit by the front facet as it is conceptually pushed through the model using a polygon-clipping algorithm;
identifying these segments, and the borders between them, in the front facet; and
classifying the segments and borders seen in the front facet as spurious features.

23. The method of claim 22, further comprising:
conceptually reflecting the segments off the back facets and pushing them through the model of the gemstone along the direction of the reflected ray;
identifying further facets hit, and segments of these facets visible in the front facet, using the polygon-clipping algorithm;
repeating the process up to a pre-defined maximum number of reflections; and
identifying all of the segments and borders between them as spurious features.

24. The method of claim 19, further comprising clustering features together to form defects.

25. The method of claim 24, wherein a bounding volume within the 3D model is determined for each defect.

26. The method of claim 25, wherein:
each bounding volume is back-projected onto all the front facets through which it is visible;
in each diffuse image, the grey-levels of pixels forming back-projections of each defect are analysed; and
statistical measures on the content of each defect are obtained.

27. The method of claim 26, wherein the grey-levels of pixels are determined relative to a map formed by the back projections of back facets of the gemstone.

28. The method of claim 26, wherein parameters of the inclusions are determined from the statistical measures.

29. Apparatus for forming a 3D model of a gemstone, comprising:
a mounting stage for mounting the gemstone, the mounting stage being rotatable in a series of discrete increments;
at least one camera directed towards the mounting stage for recording images of the gemstone at each rotationally incremented position;
a collimated light source for illuminating the diamond with collimated light;
at least one diffuse light source for illuminating the diamond with diffuse light;
a control system for co-ordinating the rotation of the mounting stage, operation of the light sources and operation of the at least one camera, so that the following steps are performed at each rotational position of the gemstone:

(a) a silhouette image of the gemstone illuminated by collimated light is recorded by the camera;

(b) a diffuse image of the gemstone illuminated by diffuse light is recorded by the camera; and a processing system arranged to analyse the silhouette images so as to obtain an initial 3D model of the surface of the gemstone, and refine the initial model using information contained in the diffuse images to obtain the 3D model.

30. The apparatus of claim 29 and adapted to identify inclusions in the gemstone, wherein the processing system is further arranged to:

identify features in the diffuse images;

track the features between subsequent diffuse images;

locate the features relative to the 3D model of the gemstone, taking into account reflection and refraction of light rays by the gemstone; and identify some or all of the located features as inclusions.

31. The apparatus of claim 29, further comprising a stepper motor for rotating the mounting stage.

32. The apparatus of claim 29, wherein the at least one camera includes a girdle camera directed towards a girdle of a gemstone mounted on the mounting stage, arranged so that the silhouette images are recorded by the girdle camera.

33. The apparatus of claim 29, further comprising a pavilion camera directed towards a pavilion of a gemstone mounted on the mounting stage.

34. Apparatus for identifying inclusions in a gemstone, comprising:

a mounting stage for mounting the gemstone, the mounting stage being rotatable in a series of discrete increments;

at least one camera directed towards the mounting stage for recording images of the gemstone at each rotationally incremented position;

a collimated light source for illuminating the diamond with collimated light;

at least one diffuse light source for illuminating the diamond with diffuse light;

a control system for co-ordinating the rotation of the mounting stage, operation of the light sources and operation of the at least one camera, so that the following steps are performed at each rotational position of the gemstone:

(a) a silhouette image of the gemstone illuminated by collimated light is recorded by the camera;

(b) a diffuse image of the gemstone illuminated by diffuse light is recorded by the camera; and a processing system arranged to:

analyse the silhouette images to obtain a 3D model of the surface of the gemstone;

identify features in the diffuse images;

track the features between subsequent diffuse images;

locate the features relative to the 3D model of the gemstone, taking into account reflection and refraction of light rays by the gemstone; and identify some or all of the located features as inclusions.

* * * * *